US008562975B2

(12) United States Patent
Ueda et al.

(10) Patent No.: US 8,562,975 B2
(45) Date of Patent: Oct. 22, 2013

(54) METHOD FOR STABILIZING REDUCED COENZYME $Q_{10}$ AND COMPOSITION THEREFOR

(75) Inventors: Yasuyoshi Ueda, Hyogo (JP); Takahiro Ueda, Hyogo (JP); Tadao Ono, Hyogo (JP); Shiro Kitamura, Hyogo (JP); Kenji Fujii, Hyogo (JP); Kazunori Hosoe, Hyogo (JP)

(73) Assignee: Kaneka Corporation, Osaka (JP)

( * ) Notice: Subject to any disclaimer, the term of this patent is extended or adjusted under 35 U.S.C. 154(b) by 849 days.

(21) Appl. No.: 10/501,698

(22) PCT Filed: Jan. 20, 2003

(86) PCT No.: PCT/JP03/00394
§ 371 (c)(1),
(2), (4) Date: Feb. 3, 2005

(87) PCT Pub. No.: WO03/062182
PCT Pub. Date: Jul. 31, 2003

(65) Prior Publication Data
US 2005/0147598 A1    Jul. 7, 2005

(30) Foreign Application Priority Data

Jan. 18, 2002  (JP) .................................... 2002-9737
Oct. 9, 2002   (JP) ................................ 2002-296802

(51) Int. Cl.
*A61K 38/43*    (2006.01)
(52) U.S. Cl.
USPC ........................................ 424/94.1; 424/455
(58) Field of Classification Search
None
See application file for complete search history.

(56) References Cited

U.S. PATENT DOCUMENTS

| | | | |
|---|---|---|---|
| 4,751,241 A * | 6/1988 | Motoyama et al. ........... | 514/532 |
| 6,156,802 A | 12/2000 | Mae et al. | |
| 6,184,255 B1 | 2/2001 | Mae et al. | |
| 6,300,377 B1 | 10/2001 | Chopra | |
| 2002/0001660 A1 | 1/2002 | Takeuchi et al. | |

FOREIGN PATENT DOCUMENTS

| | | |
|---|---|---|
| CA | 2417089 A1 | 3/2002 |
| EP | 0 659 402 A2 | 6/1995 |
| EP | 0882450 A2 | 12/1998 |
| EP | 0882450 A3 | 12/1998 |
| EP | 0 956 854 A1 | 11/1999 |
| JP | 55-81813 A | 6/1980 |
| JP | 10-109933 | 4/1998 |
| JP | 10109933 A | 4/1998 |
| JP | 10-330251 | 12/1998 |
| JP | 2000-309794 | 11/2000 |
| JP | 2003-89669 A | 3/2003 |
| JP | 2003-113129 A | 4/2003 |
| WO | WO 00/23069 | 4/2000 |
| WO | WO 01/52822 A1 | 7/2001 |
| WO | WO 02/17879 A1 | 3/2002 |
| WO | WO 02/090304 A1 | 11/2002 |

OTHER PUBLICATIONS

International Search Report From Corresponding International Application No. PCT/JP03/00394, Dated Apr. 30, 2003, 2 pages.
Patent Cooperation Treaty International Preliminary Examination Report (PCT Article 36 and Rule 70), From Corresponding International Application No. PCT/JP2003/000394, Dated Dec. 25, 2003, 7 pages.
Supplementary European Search Report from Application No. EP 03 70 0597, Jun. 21, 2006, 3 pages.

* cited by examiner

*Primary Examiner* — Jon P Weber
*Assistant Examiner* — Satyendra Singh
(74) *Attorney, Agent, or Firm* — Novak Druce Connolly Bove + Quigg LLP

(57) ABSTRACT

The present invention relates to a method for stabilizing reduced coenzyme $Q_{10}$, which is useful as an ingredient in good foods, functional nutritive foods, specific health foods, nutritional supplements, nutrients, animal drugs, drinks, feeds, cosmetics, medicines, remedies, preventive drugs, etc., and to a composition therefor. The composition comprises reduced coenzyme $Q_{10}$, a fat and oil (excluding olive oil) and/or a polyol, and doesn't substantially inhibit the stabilization of reduced coenzyme $Q_{10}$. Additionally, the composition is a reduced coenzyme $Q_{10}$-containing composition which comprises reduced coenzyme $Q_{10}$, a polyglycerol fatty acid ester, and a fat and oil and/or a polyol.

25 Claims, No Drawings

METHOD FOR STABILIZING REDUCED COENZYME $Q_{10}$ AND COMPOSITION THEREFOR

RELATED APPLICATIONS

This application is a nationalization of PCT Application No. PCT/JP03/00394 filed Jan. 20, 2003. This application claims priority from Japanese Patent Application No. 2002-9737 filed on Jan. 18, 2002 and Japanese Patent Application No. 2002-296802 filed on Oct. 9, 2002.

TECHNICAL FIELD

The present invention relates to a method for stabilizing reduced coenzyme $Q_{10}$ and to a composition in which reduced coenzyme $Q_{10}$ can be maintained stably. Reduced coenzyme $Q_{10}$ shows a higher level of oral absorbability as compared with oxidized coenzyme $Q_{10}$ and it is a compound useful as an ingredient in good foods, functional nutritive foods, specific health foods, nutritional supplements, nutrients, animal drugs, drinks, feeds, cosmetics, medicines, remedies, preventive drugs, etc.

BACKGROUND ART

It is known that reduced coenzyme $Q_{10}$ can be prepared by producing coenzyme $Q_{10}$ in such conventional manner as synthesis, fermentation, or extraction from natural products, and concentrating a reduced coenzyme $Q_{10}$-containing eluate fraction resulting from chromatography, and by the like method (JP-A-10-109933). On that occasion, as described in the above-cited publication, the chromatographic concentration may be carried out after reduction of oxidized coenzyme $Q_{10}$ contained in the reduced coenzyme $Q_{10}$ with a conventional reducing agent such as sodium borohydride or sodium dithionite (sodium hydrosulfite), or reduced coenzyme $Q_{10}$ may be prepared by reacting an existing highly pure grade of coenzyme $Q_{10}$ with the reducing agent mentioned above.

However, the thus-obtained reduced coenzyme $Q_{10}$ is not always in a highly pure state but is often in a low-purity crystalline, oily or semisolid form, which contains impurities such as oxidized coenzyme $Q_{10}$, for instance.

As a result of intensive investigations, the present inventors have established several methods of obtaining high-quality reduced coenzyme $Q_{10}$ and applied for patent (Japanese Patent Application Nos. 2002-114854, 2002-114871, 2002-114872, 2002-114873, 2002-114874, 2002-114875, 2002-114876, 2002-114877, 2002-114878, and 2002-114879).

However, reduced coenzyme $Q_{10}$ is readily oxidized to oxidized coenzyme $Q_{10}$ by molecular oxygen and, even when high-quality reduced coenzyme $Q_{10}$ is produced by such methods as those disclosed in the above-cited patent applications, it is still a big problem how to stabilize reduced coenzyme $Q_{10}$ in processing it into foods, functional nutritive foods, specific health foods, nutritional supplements, nutrients, animal drugs, drinks, feeds, cosmetics, medicines, remedies, preventive drugs, etc., or raw materials or compositions therefor and/or storing such processed products after preparation. In the above-mentioned processing or storage, it is very difficult to completely eliminate or shield against oxygen, and residual oxygen or contaminant oxygen exerts a great adverse influence upon warming in processing or during long-term storage, in particular. The above-mentioned oxidation is directly connected with such a quality problem as the formation of oxidized coenzyme $Q_{10}$ as a byproduct.

Thus, it is a very important problem to stabilize (protect against oxidation) reduced coenzyme $Q_{10}$. Since, however, reduced coenzyme $Q_{10}$ has not been commercialized up to the present, there have been few studies done on the method and composition for stably maintain reduced coenzyme $Q_{10}$. In the only example published (WO 01/52822), there are described a composition coexisting a reducing agent and preparation method thereof. Disclosed in that document are:

1) A composition which comprises reduced coenzyme $Q_{10}$, an effective amount of a reducing agent in preventing oxidation of reduced coenzyme $Q_{10}$ to oxidized coenzyme $Q_{10}$, and a surfactant or a vegetable oil or a mixture of these in an amount effective in dissolving the reduced coenzyme $Q_{10}$ and the reducing agent, optionally together with a solvent;
2) A composition for oral administration obtained by forming the above composition into a gelatin capsule or a tablet; and, further,
3) A method of preparing the above composition which contains reduced coenzyme $Q_{10}$ prepared in situ by using oxidized coenzyme $Q_{10}$ and a reducing agent.

However, the above publication WO 01/52822 has no detailed description of the quality of reduced coenzyme $Q_{10}$ contained in the composition, the stabilizing effect, or the like. Moreover, the above composition and the above method of preparation are very complicated and troublesome since the composition has to play a plurality of roles (namely, a first role as the field of reaction for reducing oxidized coenzyme $Q_{10}$ to reduced coenzyme $Q_{10}$, and a second role in stably maintaining reduced coenzyme $Q_{10}$).

Furthermore, it is to be noted that the reaction mixture itself is directly used as such in the above composition or method of preparation and, therefore, it is hard to say that the composition is always safe. More specifically, while an ascorbic acids is used as the reducing agent in reducing oxidized coenzyme $Q_{10}$ to reduced coenzyme $Q_{10}$, the composition is contaminated with significant amounts of the corresponding dehydroascorbic acid, 2,3-diketoglucuronic acid, threonic acid, oxalic acid and the like as a result of oxidation of such ascorbic acids. Unlike ascorbic acids, dehydroascorbic acids and oxalic acid resulting from decomposition are highly harmful. For example, they reportedly increase the lipid peroxide level and decrease the antioxidant substance level in the liver and kidney, and increase the oxalic acid level in the kidney and there is a fear of adverse effects, for example, decreases in resistance to oxidative stress, symptom of urolithiasis and the like (Nutrition Research, vol. 13, pp. 667-676, 1993).

As for the composition containing reduced coenzyme $Q_{10}$, the above-cited JP-A-10-109933 discloses a composition comprising 0.3 g of coenzyme $Q_{10}$ (oxidized form: reduced form=5:95) and 6.0 ml (5.45 g) of olive oil (reduced coenzyme $Q_{10}$ content in the composition=4.96% by weight) and a composition comprising 20 parts by weight of coenzyme $Q_{10}$ (oxidized form: reduced form=15:85), 15 parts by weight of vitamin E and 350 parts by weight of soybean oil (reduced coenzyme $Q_{10}$ content in the composition=4.42% by weight; vitamin E content based on the system excluding coenzyme $Q_{10}$: 4.11% by weight).

However, in the above publication, there is no description at all of the stability of reduced coenzyme $Q_{10}$, for example and, as a result of investigations made by the present inventors, it was found that the above compositions are not always preferred as compositions for stably maintaining reduced coenzyme $Q_{10}$.

SUMMARY OF THE INVENTION

In view of the above-discussed state of the art, it is an object of the present invention to provide a simple and preferable method, a composition and an oral dosage form by or in which reduced coenzyme $Q_{10}$ is protected against oxidation and maintained stably in processing it into foods, functional nutritive foods, specific health foods, nutritional supplements, nutrients, animal drugs, drinks, feeds, cosmetics, medicines, remedies, preventive drugs, etc., or raw materials or compositions therefor and/or in storing such products after preparation.

The present inventors made intensive investigations in an attempt to accomplish the above object and, as a result, found that those ingredients so far generally used in preparing foods, functional nutritive foods, specific health foods, nutritional supplements, nutrients, animal drugs, drinks, feeds, cosmetics, medicines, remedies, preventive drugs, etc., or raw materials or compositions therefor do not always favorably serve to stabilize (i.e. protect against oxidation) reduced coenzyme $Q_{10}$ and, further, that reduced coenzyme $Q_{10}$ is protected against oxidation by molecular oxygen in a surprisingly favorable manner in the presence of a fat and oil and/or a polyol without preparing any complicated and trouble-causing composition.

Furthermore, it was found that while the coexistence/addition of Tween and Span species (all being surfactants (emulsifiers)) in wide use for absorbability in the living body improvement markedly decreases the above-mentioned reduced coenzyme $Q_{10}$-stabilizing effect of fat and oil and/or polyol, the coexistence/addition of polyglycerol fatty acid esters surprisingly has little influence on the stabilizing effect of fat and oil and/or polyol and such esters serve as very favorable surfactants (emulsifiers). Based on such and other findings, the present invention has been completed.

Thus, in a first aspect, the present invention relates to
a method for stabilizing reduced coenzyme $Q_{10}$
which comprises obtaining a composition by admixing reduced coenzyme $Q_{10}$ with a fat and oil (excluding olive oil) and/or a polyol as the main component in which the stabilization of reduced coenzyme $Q_{10}$ is not substantially inhibited and thereby protecting reduced coenzyme $Q_{10}$ against oxidation.

Moreover, in a second aspect, the present invention relates to
a composition
which comprises reduced coenzyme $Q_{10}$, a fat and oil (exclusive of olive oil) and/or a polyol and in which the stabilization of reduced coenzyme $Q_{10}$ is not substantially inhibited.

Furthermore, in a third aspect, the present invention relates to
a reduced coenzyme $Q_{10}$-containing composition
which comprises reduced coenzyme $Q_{10}$, a polyglycerol fatty acid ester, and a fat and oil and/or a polyol.

In accordance with the present invention, a stable and appropriate composition containing reduced coenzyme $Q_{10}$ can be provided without purposely adding a plurality of ingredients. Furthermore, it is also possible to provide a composition following the recent nature-oriented trend, namely a reduced coenzyme $Q_{10}$-containing composition prepared (processed) using nature-derived raw materials.

DETAILED DESCRIPTION OF THE INVENTION

In the following, the present invention is described in detail. In the present specification, "coenzyme $Q_{10}$" only so referred to indicate either the oxidized form or reduced form or, when both exist in admixture, a mixture of both forms.

First, the first and second aspects of the invention are described.

In its first aspect, the invention relates to
a method for stabilizing reduced coenzyme $Q_{10}$
which comprises obtaining a composition by admixing reduced coenzyme $Q_{10}$ with a fat and oil (excluding olive oil) and/or a polyol as the main component in which the stabilization of reduced coenzyme $Q_{10}$ is not substantially inhibited and thereby protecting reduced coenzyme $Q_{10}$ against oxidation.

Moreover, in its second aspect, the invention relates to
a composition
which comprises reduced coenzyme $Q_{10}$, a fat and oil (exclusive of olive oil) and/or a polyol and in which the stabilization of reduced coenzyme $Q_{10}$ is not substantially inhibited.

Thus, in accordance with the first and second aspects of the invention, a fat and oil and/or a polyol is used for inhibiting the oxidation of reduced coenzyme $Q_{10}$ to oxidized coenzyme $Q_{10}$ by molecular oxygen.

In the practice of the invention, the reduced coenzyme $Q_{10}$ may consist of reduced coenzyme $Q_{10}$ alone or may occur as a mixture with oxidized coenzyme $Q_{10}$. In the case of such mixture, the proportion of reduced coenzyme $Q_{10}$ relative to the total amount of coenzyme $Q_{10}$ (namely, the total amount of reduced coenzyme $Q_{10}$ and oxidized coenzyme $Q_{10}$) is not particularly restricted but is, for example, not lower than 20% by weight, preferably not lower than 40% by weight, more preferably not lower than 60% by weight, still more preferably not lower than 80%, further preferably not lower than 90%, particularly preferably not lower than 96% by weight. The upper limit is, but is not particularly restricted to, 100% by weight and, generally, that proportion is not higher than 99.9%.

The fat and oil and/or the polyol is preferably one acceptable for food or pharmaceutical use.

The fat and oil may be a natural animal or vegetable fat and oil, a synthetic fat and oil, or a modified fat and oil. As the vegetable fat and oil, there may be mentioned, for example, coconut oil, palm oil, palm kernel oil, linseed oil, camellia oil, brown rice germ oil, avocado oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil and the like, and as the animal fat and oil, there may be mentioned, for example, lard, milk fat, fish oil, beef tallow and the like. There may further be mentioned modifications (e.g. hydrogenated oils) derived from these by fractionation, hydrogenation, transesterification or the like. It is of course possible to use medium-chain fatty acid triglycerides (MCT), fatty acid partial glycerides, phospholipids and the like. These may be used singly or two or more of them may be used in combination.

As the medium-chain fatty acid triglycerides, there may be mentioned, for example, $C_6$-$C_{12}$ (preferably $C_8$-$C_{12}$) fatty acid triglycerides, and the like. As the fatty acid partial glycerides, there may be mentioned, for example, $C_6$-$C_{18}$ (preferably $C_6$-$C_{12}$) fatty acid monoglycerides and diglycerides, and the like. As the phospholipids, there may be mentioned lecithin, and the like, for example.

Among the above-mentioned fats and oils, vegetable fat and oil, synthetic fat and oil, and modified fat and oil are preferred from the ease of handling, odor and/or the like viewpoint. The fat and oil to be used is preferably selected considering the cost thereof, the stability of reduced coenzyme $Q_{10}$ therein and the solubility of coenzyme $Q_{10}$ therein, for instance. Thus, for example, coconut oil, palm oil, palm kernel oil, rapeseed oil, rice oil, soybean oil, cottonseed oil, MCT and the like are preferred, and rice oil, soybean oil, rapeseed oil, MCT and the like are more preferred. From the viewpoint of solubility of coenzyme $Q_{10}$ and/or absorbability in the living body, for example, MCT can be used most preferably.

Olive oil is a little inferior in reduced coenzyme $Q_{10}$-stabilizing effect (protective effect against oxidation) to other fats and oils.

As for the polyol, those polyols which are safe and suited for food or pharmaceutical use, for example, glycerol, propylene glycol, polyethylene glycols (preferably polyethylene glycols having a molecular weight of 300 to 1,000) and the like, are preferably used. These may be used singly or two or more of them may be used in combination. In particular, glycerol can be used favorably.

The above-mentioned fat and oil and polyol may be used singly, or mixtures of two or more of the fats and oils, mixtures of two or more of the polyols, or mixtures of the fat and oil and polyol may also be used.

In the composition mentioned above, the proportions of the fat and oil and polyol is not particularly restricted but, in view of the solubility of coenzyme $Q_{10}$, the weight ratio fat and oil/(fat and oil+polyol) is generally not lower than 1/10, preferably not lower than 1/5, more preferably not lower than 1/2, still more preferably not lower than 2/3. It goes without saying that the polyol-free case is also appropriate.

The above composition contains reduced coenzyme $Q_{10}$ and comprises the fat and oil and/or polyol as the main component, and the content of the fat and oil and/or polyol is preferably high. That content is not particularly restricted but not lower than 50% by weight, preferably not lower than 60% by weight, more preferably not lower than 70% by weight, still more preferably not lower than 80%, particularly preferably not lower than 85% by weight, based on the system excluding coenzyme $Q_{10}$.

The phrase "based on the system excluding coenzyme $Q_{10}$" as used herein means that the basis is the total weight of the composition minus the weight of coenzyme $Q_{10}$.

In the above composition, reduced coenzyme $Q_{10}$ is generally in a dissolved or suspended state and, according to fat and oil and/or polyol species employed, the composition may take the form of a liquid or solid or slurry.

Furthermore, the above composition may be consist of reduced coenzyme $Q_{10}$, a fat and oil and/or polyol alone, or may further contain another or other ingredients. When it further contains another or other fat and oil ingredients, the composition is preferably formulated so that the stabilization of reduced coenzyme $Q_{10}$ by the fat and oil and/or polyol may not be substantially inhibited.

For example, vitamin E is an ingredient generally and frequently used as a stabilizer or antioxidant but it was confirmed that when the content thereof is high (4.11% by weight based on the system excluding coenzyme $Q_{10}$), as in the composition described in the above-cited JP-A-10-109933, it inhibits the stabilization of reduced coenzyme $Q_{10}$. Therefore, vitamin E is not an essential constituent of the composition of the invention. When vitamin E is used according to the intended use of the composition, its content should be minimized to a level lower than 4% by weight based on the system excluding coenzyme $Q_{10}$.

It was also confirmed that the coexistence of Tween and Span species as surfactants (emulsifiers) inhibits the stabilization of reduced coenzyme $Q_{10}$, as mentioned hereinabove. Therefore, these are not essential constituents in the practice of the invention, either. When these are to be used according to the intended use of the composition, the content thereof is preferably restricted to a necessary lowest level, for example a total content of Tween and Span species of generally not higher than 30% by weight, preferably not higher than 20% by weight, more preferably not higher than 10% by weight, based on the system excluding coenzyme $Q_{10}$.

It is of course allowable to add one or more ingredients incapable of substantially inhibiting the stabilization of reduced coenzyme $Q_{10}$ in an amount or amounts in which the stabilization is not substantially inhibited, and there may be a large number of such ingredients. From this viewpoint, the present invention described above defines, as the gist thereof, a composition which comprises reduced coenzyme $Q_{10}$ and, as the main component(s), one or more fat and oil (excluding olive oil) and/or one or more polyol and in which the stabilization of reduced coenzyme $Q_{10}$ is not substantially inhibited. It is a matter of course that the simplest constitution of the present invention described above consists in a composition comprising reduced coenzyme $Q_{10}$ and one or more fat and oil and/or one or more polyol alone as well as a method for stabilizing reduced coenzyme $Q_{10}$ by employing such constitution.

The phrase "the stabilization of reduced coenzyme $Q_{10}$ is not substantially inhibited" as used herein means that the other constituent(s) or ingredient(s) other than the fat and oil and/or polyol will not impair the original oxidation-inhibiting effect of the fat and oil and/or polyol by 5% or less. Thus, it means that when a composition comprising reduced coenzyme $Q_{10}$, one or more fat and oil and/or one or more polyol and, in addition, one or more ingredients other than the fat and oil and/or polyol is stored in the air at 40° C. under light-shielding conditions for 3 days, the relative residual percentage of reduced coenzyme $Q_{10}$ is not lower than 95%, preferably not lower than 96%, more preferably not lower than 97%, with the residual percentage of reduced coenzyme $Q_{10}$ as found by storing, under the same conditions, the corresponding composition containing no ingredients other than the fat and oil and/or polyol being taken as 100%.

In accordance with the first and second aspects of the invention, an ingredient having reducing activity may be added according to the intended purpose. Unlike the conventional compositions, however, the composition of the invention can stably maintain reduced coenzyme $Q_{10}$ even when it contains no such reducing agent.

Now, the third aspect of the invention is described. The third aspect of the invention is concerned with a reduced coenzyme $Q_{10}$-containing composition which comprises reduced coenzyme $Q_{10}$, a polyglycerol fatty acid ester and a fat and oil and/or a polyol.

In accordance with the third aspect of the invention, a fat and oil and/or a polyol is used for inhibiting the oxidation of reduced coenzyme $Q_{10}$ to oxidized coenzyme $Q_{10}$ by molecular oxygen and, further, a polyglycerol fatty acid ester is used as a surfactant (emulsifier) capable of satisfactorily maintaining the stabilizing effect (protective effect against oxidation) of the fat and oil and/or polyol. Polyglycerol fatty acid esters constitute a class of glycerol fatty acid esters but, unlike the cases where monoglycerol fatty acid esters (including organic acid monoglycerides) or other glycerol fatty acid esters such as polyglycerol condensed ricinolic acid esters, they can contribute to the stabilization of reduced coenzyme $Q_{10}$ and high-level in absorbability in the living body thereof simultaneously.

In the practice of the invention, the reduced coenzyme $Q_{10}$ may consist of reduced coenzyme $Q_{10}$ alone or may occur as a mixture with oxidized coenzyme $Q_{10}$. In the case of such mixture, the proportion of reduced coenzyme $Q_{10}$ relative to the total amount of coenzyme $Q_{10}$ (namely, the total amount of reduced coenzyme $Q_{10}$ and oxidized coenzyme $Q_{10}$) is not particularly restricted but is, for example, not lower than 20% by weight, preferably not lower than 40% by weight, more preferably not lower than 60% by weight, still more preferably not lower than 80%, further preferably not lower than 90%, particularly preferably not lower than 96% by weight. The upper limit is, but is not particularly restricted to, 100% by weight and, generally, that proportion is not higher than 99.9%.

The polyglycerol fatty acid ester which can be used in the practice of the invention is represented by the formula (1):

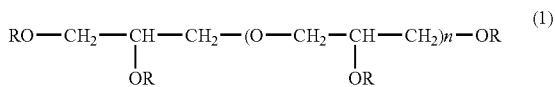

in the formula, n represents an integer of 1 to 29 and the four R's each independently represents a fatty acid residue containing 2 to 22 carbon atoms or a hydrogen atom, exclusive of the case where all R's are hydrogen atoms. Thus, the only restriction to the polyglycerol fatty acid ester represented by the above formula (1) is that the number of fatty acid residues is not smaller than 1.

Preferably, the ratio between the number of fatty acid residues in the polyglycerol fatty acid ester and the degree of polymerization of glycerol is about ¼ to about ½. The term "degree of polymerization of glycerol" as used herein means the number of glycerol molecules polymerized. In the case of diglycerol monocaprylate, for instance, the number of fatty acid residues is 1 (mono) and the degree of polymerization of glycerol is 2 (di), hence the above ratio is ½. When there are two or more fatty acid residues occur in the above formula (1), the fatty acid residues may be the same or different. From the ready availability and the like viewpoint, however, those esters in which they are the same are generally preferred.

The polyglycerol fatty acid ester is not particularly restricted but, in view of the stability and absorbability of reduced coenzyme $Q_{10}$, one having an HLB value within the range the lower limit of which is generally not lower than 4, preferably not lower than 5, more preferably not lower than 6, still more preferably not lower than 7, particularly preferably not lower than 8 and the upper limit of which is generally not higher than 12, preferably not higher than 11, more preferably not higher than 10.

As specific examples of the polyglycerol fatty acid ester, there may be mentioned, for example, diglycerol monocaprylate, diglycerol dicaprylate, diglycerol tricaprylate, diglycerol tetracaprylate, triglycerol monocaprylate, triglycerol dicaprylate, triglycerol tricaprylate, triglycerol tetracaprylate, triglycerol pentacaprylate, tetraglycerol monocaprylate, tetraglycerol dicaprylate, tetraglycerol tricaprylate, tetraglycerol tetracaprylate, tetraglycerol pentacaprylate, tetraglycerol hexacaprylate, pentaglycerol monocaprylate, pentaglycerol dicaprylate, pentaglycerol tricaprylate, pentaglycerol tetracaprylate, pentaglycerol pentacaprylate, pentaglycerol hexacaprylate, pentaglycerol heptacaprylate, hexaglycerol monocaprylate, hexaglycerol dicaprylate, hexaglycerol tricaprylate, hexaglycerol tetracaprylate, hexaglycerol pentacaprylate, hexaglycerol hexacaprylate, hexaglycerol heptacaprylate, hexaglycerol octacaprylate, heptaglycerol monocaprylate, heptaglycerol dicaprylate, heptaglycerol tricaprylate, heptaglycerol tetracaprylate, heptaglycerol pentacaprylate, heptaglycerol hexacaprylate, heptaglycerol heptacaprylate, heptaglycerol octacaprylate, heptaglycerol nonacaprylate, octaglycerol monocaprylate, octaglycerol dicaprylate, octaglycerol tricaprylate, octaglycerol tetracaprylate, octaglycerol pentacaprylate, octaglycerol hexacaprylate, octaglycerol heptacaprylate, octaglycerol octacaprylate, octaglycerol nonacaprylate, octaglycerol decacaprylate, nonaglycerol monocaprylate, nonaglycerol dicaprylate, nonaglycerol tricaprylate, nonaglycerol tetracaprylate, nonaglycerol pentacaprylate, nonaglycerol hexacaprylate, nonaglycerol heptacaprylate, nonaglycerol octacaprylate, nonaglycerol nonacaprylate, nonaglycerol decacaprylate, nonaglycerol undecacaprylate, decaglycerol monocaprylate, decaglycerol dicaprylate, decaglycerol tricaprylate, decaglycerol tetracaprylate, decaglycerol pentacaprylate, decaglycerol hexacaprylate, decaglycerol heptacaprylate, decaglycerol octacaprylate, decaglycerol nonacaprylate, decaglycerol decacaprylate, decaglycerol undecacaprylate, decaglycerol dodecacaprylate, diglycerol monocaprate, diglycerol dicaprate, diglycerol tricaprate, diglycerol tetracaprate, triglycerol monocaprate, triglycerol dicaprate, triglycerol tricaprate, triglycerol tetracaprate, triglycerol pentacaprate, tetraglycerol monocaprate, tetraglycerol dicaprate, tetraglycerol tricaprate, tetraglycerol tetracaprate, tetraglycerol pentacaprate, tetraglycerol hexacaprate, pentaglycerol monocaprate, pentaglycerol dicaprate, pentaglycerol tricaprate, pentaglycerol tetracaprate, pentaglycerol pentacaprate, pentaglycerol hexacaprate, pentaglycerol heptacaprate, hexaglycerol monocaprate, hexaglycerol dicaprate, hexaglycerol tricaprate, hexaglycerol tetracaprate, hexaglycerol pentacaprate, hexaglycerol hexacaprate, hexaglycerol heptacaprate, hexaglycerol octacaprate, heptaglycerol monocaprate, heptaglycerol dicaprate, heptaglycerol tricaprate, heptaglycerol tetracaprate, heptaglycerol pentacaprate, heptaglycerol hexacaprate, heptaglycerol heptacaprate, heptaglycerol octacaprate, heptaglycerol nonacaprate, octaglycerol monocaprate, octaglycerol dicaprate, octaglycerol tricaprate, octaglycerol tetracaprate, octaglycerol pentacaprate, octaglycerol hexacaprate, octaglycerol heptacaprate, octaglycerol octacaprate, octaglycerol nonacaprate, octaglycerol decacaprate, nonaglycerol monocaprate, nonaglycerol dicaprate, nonaglycerol tricaprate, nonaglycerol tetracaprate, nonaglycerol pentacaprate, nonaglycerol hexacaprate, nonaglycerol heptacaprate, nonaglycerol octacaprate, nonaglycerol nonacaprate, nonaglycerol decacaprate, nonaglycerol undecacaprate, decaglycerol monocaprate, decaglycerol dicaprate, decaglycerol tricaprate, decaglycerol tetracaprate, decaglycerol pentacaprate, decaglycerol hexacaprate, decaglycerol heptacaprate, decaglycerol octacaprate, decaglycerol nonacaprate, decaglycerol decacaprate, decaglycerol undecacaprate, decaglycerol dodecacaprate, diglycerol monolaurate, diglycerol dilaurate, diglycerol trilaurate, diglycerol tetralaurate, triglycerol monolaurate, triglycerol dilaurate, triglycerol trilaurate, triglycerol tetralaurate, triglycerol pentalaurate, tetraglycerol monolaurate, tetraglycerol dilaurate, tetraglycerol trilaurate, tetraglycerol tetralaurate, tetraglycerol pentalaurate, tetraglycerol hexylaurate, pentaglycerol monolaurate, pentaglycerol dilaurate, pentaglycerol trilaurate, pentaglycerol tetralaurate, pentaglycerol pentalaurate, pentaglycerol hexylaurate, pentaglycerol heptalaurate, hexaglycerol monolaurate, hexaglycerol dilaurate, hexaglycerol trilaurate, hexaglycerol tetralaurate, hexaglycerol pentalaurate, hexaglycerol hexylaurate, hexaglycerol heptalaurate, hexaglycerol octalaurate, heptaglycerol monolaurate, heptaglycerol dilaurate, heptaglycerol trilaurate, heptaglycerol tetralaurate, heptaglycerol pentalaurate, heptaglycerol hexylaurate, heptaglycerol heptalaurate, heptaglycerol octalaurate, heptaglycerol nonalaurate, octaglycerol monolaurate, octaglycerol dilaurate, octaglycerol trilaurate, octaglycerol tetralaurate, octaglycerol pentalaurate, octaglycerol hexylaurate, octaglycerol heptalaurate, octaglycerol octalaurate, octaglycerol nonalaurate, octaglycerol decalaurate, nonaglycerol monolaurate, nonaglycerol dilaurate, nonaglycerol trilaurate, nonaglycerol tetralaurate, nonaglycerol pentalaurate, nonaglycerol hexylaurate, nonaglycerol heptalaurate, nonaglycerol octalaurate, nonaglycerol nonalaurate, nonaglycerol decalaurate, nonaglycerol undecalaurate, decaglycerol monolaurate, decaglycerol dilaurate, decaglycerol trilaurate, decaglycerol tetralaurate, decaglycerol pentalaurate, decaglycerol hexylaurate, decaglycerol heptalaurate, decaglycerol octalaurate, decaglycerol nonalaurate, decaglycerol decalaurate, decaglycerol undecalaurate, decaglycerol dodecalaurate, diglycerol monomyristate, diglycerol dimyristate, diglycerol trimyristate, diglycerol tetramyristate, triglycerol monomyristate, triglycerol dimyristate, triglycerol trimyristate, triglycerol tetramyristate, triglycerol pentamyristate, tetraglycerol monomyristate, tetraglycerol dimyristate, tetraglycerol trimyristate, tetraglycerol tetramyristate, tetraglycerol pentamyristate, tetraglycerol hexamyristate, pentaglycerol monomyristate, pentaglycerol dimyristate, pentaglycerol trimyristate, pentaglycerol tetramyristate, pentaglycerol pentamyristate, pentaglycerol hexamyristate, pentaglycerol heptamyristate, hexaglycerol monomyristate, hexaglycerol dimyristate, hexaglycerol trimyristate, hexaglycerol tetramyristate, hexaglycerol pentamyristate, hexaglycerol hexamyristate, hexaglycerol heptamyristate, hexaglycerol octamyristate, heptaglycerol monomyristate, heptaglycerol dimyristate, heptaglycerol trimyristate, heptaglycerol tetramyristate, heptaglycerol pentamyristate, heptaglycerol hexamyristate, heptaglycerol heptamyristate, heptaglycerol octamyristate, heptaglycerol nonamyristate, octaglycerol monomyristate, octaglycerol dimyristate, octaglycerol trimyristate, octaglycerol tetramyristate, octaglycerol pentamyristate, octaglycerol hexamyristate, octaglycerol heptamyristate, octaglycerol octamyristate, octaglycerol nonamyristate, octaglycerol decamyristate, nonaglycerol monomyristate, nonaglycerol dimyristate, nonaglycerol trimyristate, nonaglycerol tetramyristate, nonaglycerol pentamyristate, nonaglycerol hexamyristate, nonaglycerol heptamyristate, nonaglycerol octamyristate, nonaglycerol nonamyristate, nonaglycerol decamyristate, nonaglycerol undecamyristate, decaglycerol monomyristate, decaglycerol dimyristate, decaglycerol trimyristate, decaglycerol tetramyristate, decaglycerol pentamyristate, decaglycerol hexamyristate, decaglycerol heptamyristate, decaglycerol octamyristate, decaglycerol nonamyristate, decaglycerol decamyristate, decaglycerol undecamyristate, decaglycerol dodecamyristate, diglycerol monopalmitate, diglycerol dipalmitate, diglycerol tripalmitate, diglycerol tetrapalmitate, triglycerol monopalmitate, triglycerol dipalmitate, triglycerol tripalmitate, triglycerol tetrapalmitate, triglycerol pentapalmitate, tetraglycerol monopalmitate, tetraglycerol dipalmitate, tetraglycerol tripalmitate, tetraglycerol tetrapalmitate, tetraglycerol pentapalmitate, tetraglycerol hexapalmitate, pentaglycerol monopalmitate, pentaglycerol dipalmitate, pentaglycerol tripalmitate, pentaglycerol tetrapalmitate, pentaglycerol pentapalmitate, pentaglycerol hexapalmitate, pentaglycerol heptapalmitate, hexaglycerol monopalmitate, hexaglycerol dipalmitate, hexaglycerol tripalmitate, hexaglycerol tetrapalmitate, hexaglycerol pentapalmitate, hexaglycerol hexapalmitate, hexaglycerol heptapalmitate, hexaglycerol octapalmitate, heptaglycerol monopalmitate, heptaglycerol dipalmitate, heptaglycerol tripalmitate, heptaglycerol tetrapalmitate, heptaglycerol pentapalmitate, heptaglycerol hexapalmitate, heptaglycerol heptapalmitate, heptaglycerol octapalmitate, heptaglycerol nonapalmitate, octaglycerol monopalmitate, octaglycerol dipalmitate, octaglycerol tripalmitate, octaglycerol tetrapalmitate, octaglycerol pentapalmitate, octaglycerol hexapalmitate, octaglycerol heptapalmitate, octaglycerol octapalmitate, octaglycerol nonapalmitate, octaglycerol decapalmitate, nonaglycerol monopalmitate, nonaglycerol dipalmitate, nonaglycerol tripalmitate, nonaglycerol tetrapalmitate, nonaglycerol pentapalmitate, nonaglycerol hexapalmitate, nonaglycerol heptapalmitate, nonaglycerol octapalmitate, nonaglycerol nonapalmitate, nonaglycerol decapalmitate, nonaglycerol undecapalmitate, decaglycerol monopalmitate, decaglycerol dipalmitate, decaglycerol tripalmitate, decaglycerol tetrapalmitate, decaglycerol pentapalmitate, decaglycerol hexapalmitate, decaglycerol heptapalmitate, decaglycerol octapalmitate, decaglycerol nonapalmitate, decaglycerol decapalmitate, decaglycerol undecapalmitate, decaglycerol dodecapalmitate, diglycerol monostearate, diglycerol distearate, diglycerol tristearate, diglycerol tetrastearate, triglycerol monostearate, triglycerol distearate, triglycerol tristearate, triglycerol tetrastearate, triglycerol pentastearate, tetraglycerol monostearate, tetraglycerol distearate, tetraglycerol tristearate, tetraglycerol tetrastearate, tetraglycerol pentastearate, tetraglycerol hexastearate, pentaglycerol monostearate, pentaglycerol distearate, pentaglycerol tristearate, pentaglycerol tetrastearate, pentaglycerol pentastearate, pentaglycerol hexastearate, pentaglycerol heptastearate, hexaglycerol monostearate, hexaglycerol distearate, hexaglycerol tristearate, hexaglycerol tetrastearate, hexaglycerol pentastearate, hexaglycerol hexastearate, hexaglycerol heptastearate, hexaglycerol octastearate, heptaglycerol monostearate, heptaglycerol distearate, heptaglycerol tristearate, heptaglycerol tetrastearate, heptaglycerol pentastearate, heptaglycerol hexastearate, heptaglycerol heptastearate, heptaglycerol octastearate, heptaglycerol nonastearate, octaglycerol monostearate, octaglycerol distearate, octaglycerol tristearate, octaglycerol tetrastearate, octaglycerol pentastearate, octaglycerol hexastearate, octaglycerol heptastearate, octaglycerol octastearate, octaglycerol nonastearate, octaglycerol decastearate, nonaglycerol monostearate, nonaglycerol distearate, nonaglycerol tristearate, nonaglycerol tetrastearate, nonaglycerol pentastearate, nonaglycerol hexastearate, nonaglycerol heptastearate, nonaglycerol octastearate, nonaglycerol nonastearate, nonaglycerol decastearate, nonaglycerol undecastearate, decaglycerol monostearate, decaglycerol distearate, decaglycerol tristearate, decaglycerol tetrastearate, decaglycerol pentastearate, decaglycerol hexastearate, decaglycerol heptastearate, decaglycerol octastearate, decaglycerol nonastearate, decaglycerol decastearate, decaglycerol undecastearate, decaglycerol dodecastearate, diglycerol monooleate, diglycerol dioleate, diglycerol trioleate, diglycerol tetraoleate, triglycerol monooleate, triglycerol dioleate, triglycerol trioleate, triglycerol tetraoleate, triglycerol pentaoleate, tetraglycerol monooleate, tetraglycerol dioleate, tetraglycerol trioleate, tetraglycerol tetraoleate, tetraglycerol pentaoleate, tetraglycerol hexaoleate, pentaglycerol monooleate, pentaglycerol dioleate, pentaglycerol trioleate, pentaglycerol tetraoleate, pentaglycerol pentaoleate, pentaglycerol hexaoleate, pentaglycerol heptaoleate, hexaglycerol monooleate, hexaglycerol dioleate, hexaglycerol trioleate, hexaglycerol tetraoleate, hexaglycerol pentaoleate, hexaglycerol hexaoleate, hexaglycerol heptaoleate, hexaglycerol octaoleate, heptaglycerol monooleate, heptaglycerol dioleate, heptaglycerol trioleate, heptaglycerol tetraoleate, heptaglycerol pentaoleate, heptaglycerol hexaoleate, heptaglycerol heptaoleate, heptaglycerol octaoleate, heptaglycerol nonaoleate, octaglycerol monooleate, octaglycerol dioleate, octaglycerol trioleate, octaglycerol tetraoleate, octaglycerol pentaoleate, octaglycerol hexaoleate, octaglycerol heptaoleate, octaglycerol octaoleate, octaglycerol nonaoleate, octaglycerol decaoleate, nonaglycerol monooleate, nonaglycerol dioleate, nonaglycerol trioleate, nonaglycerol tetraoleate, nonaglycerol pentaoleate, nonaglycerol hexaoleate, nonaglycerol heptaoleate, nonaglycerol octaoleate, nonaglycerol nonaoleate, nonaglycerol decaoleate, nonaglycerol undecaoleate, decaglycerol monooleate, decaglycerol dioleate, decaglycerol trioleate, decaglycerol tetraoleate, decaglycerol pentaoleate, decaglycerol hexaoleate, decaglycerol heptaoleate, decaglycerol octaoleate, decaglycerol nonaoleate, decaglycerol decaoleate, decaglycerol undecaoleate, decaglycerol dodecaoleate, etc.

Preferred among them are diglycerol monocaprate, diglycerol monolaurate, tetraglycerol monolaurate, pentaglycerol monomyristate, pentaglycerol trimyristate, diglycerol monostearate, tetraglycerol monostearate, tetraglycerol tristearate, tetraglycerol pentastearate, hexaglycerol monostearate, hexaglycerol distearate, hexaglycerol tristearate, hexaglycerol pentastearate, decaglycerol distearate, decaglycerol tristearate, diglycerol monooleate, diglycerol dioleate, tetraglycerol monooleate, hexaglycerol monooleate, hexaglycerol pentaoleate, decaglycerol trioleate, and decaglycerol pentaoleate. More preferred are diglycerol monocaprate, diglycerol monolaurate, tetraglycerol monolaurate, diglycerol monooleate, diglycerol dioleate, tetraglycerol monooleate, and decaglycerol pentaoleate. Still more preferred are diglycerol monocaprate, diglycerol monolaurate, and diglycerol monooleate. Particularly preferred is diglycerol monooleate.

When these polyglycerol fatty acid esters are used, reduced coenzyme $Q_{10}$ can be stably maintained in the presence of a fat and oil and/or a polyol, unlike the cases where monoglycerol fatty acid esters (including organic acid monoglycerides), polyglycerol condensed ricinolic acid esters or the like are used, as described hereinabove.

When the composition of the invention is intended to use in foods, those polyglycerol fatty acid esters in which the fatty acid residue or residues contain 8 or more carbon atoms and thus are ones derived from caprylic acid or a fatty acid longer in chain length than caprylic acid are preferred among the polyglycerol fatty acid esters enumerated above. The degree of polymerization of glycerol in the polyglycerol fatty acid ester is preferably not higher than 10, and diglycerol fatty acid esters in which that degree of polymerization is 2 are more preferred.

The coexistence/addition of the above-mentioned polyglycerol fatty acid esters hardly inhibits the stabilizing effect of the fat and oil and/or polyol. Therefore, their content is not particularly restricted but the lower limit thereto, based on the system excluding coenzyme $Q_{10}$, is, for example, generally not lower than 1% by weight, preferably not lower than 2% by weight, more preferably not lower than 3% by weight, still more preferably not lower than 5% by weight, and the upper limit in view of the economic feature, and the like, is generally not higher than 50% by weight, preferably not higher than 40% by weight, more preferably not higher than 30% by weight, still more preferably not higher than 20% by weight, particularly preferably not higher than 10% by weight. It is of course possible to employ content levels outside the range mentioned above according to need.

The fat and oil and/or the polyol to be used in the practice of the invention is preferably one acceptable for food or pharmaceutical use.

The fat and oil may be a natural animal or vegetable fat and oil, a synthetic fat and oil, or a modified fat and oil. As the vegetable fat and oil, there may be mentioned, for example, coconut oil, palm oil, palm kernel oil, linseed oil, camellia oil, brown rice germ oil, avocado oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil, olive oil and the like, and as the animal fat and oil, there may be mentioned, for example, lard, milk fat, fish oil, beef tallow and the like. There may further be mentioned modifications (e.g. hydrogenated oils) derived from these by fractionation, hydrogenation, transesterification or the like. It is of course possible to use medium-chain fatty acid triglycerides (MCT), fatty acid partial glycerides, phospholipids and the like. These may be used singly or two or more of them may be used in combination.

As the medium-chain fatty acid triglycerides, there may be mentioned, for example, $C_6$-$C_{12}$ (preferably $C_8$-$C_{12}$) fatty acid triglycerides, and the like. As the fatty acid partial glycerides, there may be mentioned, for example, $C_6$-$C_{18}$ (preferably $C_6$-$C_{12}$) fatty acid monoglycerides and diglycerides, and the like. As the phospholipids, there may be mentioned lecithin, and the like, for example.

Among the above-mentioned fats and oils, vegetable fat and oil, synthetic fat and oil, and modified fat and oil are preferred from the ease of handling, odor and/or the like viewpoint. The fat and oil to be used is preferably selected considering the cost thereof, the stability of reduced coenzyme $Q_{10}$ therein and the solubility of coenzyme $Q_{10}$ therein, for instance. Thus, for example, coconut oil, palm oil, palm kernel oil, rapeseed oil, rice oil, soybean oil, cottonseed oil, MCT and the like are preferred, and rice oil, soybean oil, rapeseed oil, MCT and the like are more preferred. From the viewpoint of solubility of coenzyme $Q_{10}$ and/or absorbability in the living body, MCT can be used most preferably.

As described above referring to the first and second aspects of the invention, olive oil is a little inferior in reduced coenzyme $Q_{10}$-stabilizing effect to other fats and oils. However, its improving effect on the absorbability in the living body of reduced coenzyme $Q_{10}$ in the presence of polyglycerol fatty acid esters is markedly high as compared with that of Tween and Span species and its inhibitory effect on the stabilization of reduced coenzyme $Q_{10}$ by polyglycerol fatty acid esters is very slight as compared with Tween and Span species. Therefore, even when olive oil is used as the fat and oil, such improving effect on the absorbability in the living body of reduced coenzyme $Q_{10}$ that more than offsets the above-mentioned some demerits of olive oil can be obtained. From this viewpoint, olive oil, too, can satisfactorily be used as a suitable fat and oil in the practice of the invention in accordance with the third aspect thereof.

As for the polyol, those polyols which are safe and suited for food or pharmaceutical use, for example glycerol, propylene glycol, polyethylene glycols (preferably polyethylene glycols having a molecular weight of 300 to 1,000) and the like, are preferably used. These may be used singly or two or more of them may be used in combination. In particular, glycerol can be used favorably.

The above-mentioned fat and oil and polyol may be used singly, or mixtures of two or more of the fats and oils, mixtures of two or more of the polyols, or mixtures of the fat and oil and polyol may also be used.

In the composition mentioned above, the proportions of the fat and oil and polyol is not particularly restricted but, in view of the solubility of coenzyme $Q_{10}$, the weight ratio fat and oil/(fat and oil+polyol) is generally not lower than $1/10$, preferably not lower than $1/5$, more preferably not lower than $1/2$, still more preferably not lower than $2/3$. It goes without saying that the polyol-free case is also appropriate.

Furthermore, ascorbic acids or, fruit juice concentrates (extracts, powders, etc.) containing ascorbic acids, for example lemon, orange, grapefruit and the like concentrates, may be added to the composition as nutrient components and the like, for instance, according to the intended use of the composition. In this case, phospholipids or phospholipid-containing fat and oil are preferably used as the fat and oil from the viewpoint of improved stability of reduced coenzyme $Q_{10}$, and the phospholipids are preferably in liquid form.

The ascorbic acids are not particularly restricted but there may be mentioned, for example, ascorbic acid, rhamnoascorbic acid, araboascrobic acid, glucoascorbic acid, fucoascorbic acid, glucoheptoascorbic acid, xyloascorbic acid, galactoascorbic acid, guloascorbic acid, alloascorbic acid, erythroascorbic acid, 6-desoxyascribic acid, and compounds similar thereto, and these may be in the form of esters or salts. These may be in the L or D or recemic form. These may be used singly or two or more of them may be used in combination.

Specifically, there may be mentioned L-ascorbic acid, L-ascorbyl palmitate, L-ascorbyl stearate, L-ascorbyl dipalmitate, sodium L-ascorbate, calcium L-ascorbate, D-araboascorbic acid and the like. In view of the solubility in fat and oil and/or polyol, L-ascorbyl palmitate, L-ascorbyl stearate and L-ascorbyl dipalmitate are preferred.

The content of the above ascorbic acids is not particularly restricted but, in view of economic features as well, it is generally not higher than 30% by weight, preferably not higher than 20% by weight, more preferably not higher than 10% by weight, particularly preferably not higher than 5% by weight, based on the system excluding coenzyme $Q_{10}$.

When ascorbic acids or a fruit juice concentrate containing ascorbic acids are added, the inhibitory effect of the coexistence of a Tween or Span species on the stabilization of reduced coenzyme $Q_{10}$ is lessened even upon further addition of a Tween or Span species as a surfactant (emulsifier) other than polyglycerol fatty acid esters and, therefore, a composition in which the stabilization and high in absorbability in the living body of reduced coenzyme $Q_{10}$ are simultaneously attained can be obtained.

In such case, the content of Tween, Span and/or the like species as surfactants (emulsifiers) other than polyglycerol fatty acid esters is not particularly restricted, either. Generally, however, it is generally not higher than 90% by weight, preferably not higher than 70% by weight, more preferably not higher than 50% by weight, still more preferably not higher than 30%, particularly preferably not higher than 10% by weight, based on the system excluding reduced coenzyme $Q_{10}$.

In cases where an ascorbic acid is added, as mentioned above, the content of the fat and oil and/or polyol in the composition of the invention is generally not lower than 10% by weight, preferably not lower than 30% by weight, more preferably not lower than 50% by weight, based on the system excluding reduced coenzyme $Q_{10}$. In cases where no ascorbic acid is added, compositions having a high fat and oil and/or polyol content are preferred. That content is not particularly restricted but, generally, it is not lower than 50% by weight, preferably not lower than 60% by weight, more preferably not lower than 70% by weight, still more preferably not lower than 80%, particularly preferably not lower than 85% by weight, based on the system excluding reduced coenzyme $Q_{10}$.

The polyglycerol fatty acid ester-containing composition mentioned above is preferably a self-emulsifiable composition which brings about an emulsified state without vigorous stirring (for example upon stirring with a glass rod), when mixed with water (for example when 50 g of the composition is mixed with 50 g of water). By selecting the polyglycerol fatty acid ester species, the other contents of such as the fat and oil, and the proportions thereof, it is possible to accomplish the above objects (stabilization of reduced coenzyme $Q_{10}$ and high in absorbability in the living body).

The extent of stabilization of reduced coenzyme $Q_{10}$ to be attained in accordance with the third aspect of the invention is not particularly restricted but, for example, the percent retention of reduced coenzyme $Q_{10}$ as determined by storing the composition containing reduced coenzyme $Q_{10}$, a fat and oil and/or a polyol and further a polyglycerol fatty acid ester in the air at 40° C. in a condition shielded against light for 3 days is not smaller than 70%, preferably not smaller than 80%, still more preferably not smaller than 90%, with the retention obtained by storing the corresponding composition containing reduced coenzyme $Q_{10}$, the fat and oil and/or polyol alone under the same conditions being taken as 100%. As described hereinabove, it goes without saying that compositions in which the reduced coenzyme $Q_{10}$-stabilizing effect is not substantially inhibited are desirable.

In the above manner, the stabilization and high in absorbability in the living body of reduced coenzyme $Q_{10}$ can be achieved simultaneously in accordance with the third aspect of the invention.

The essential factors in the first and second aspects of the invention described hereinabove may be applied as other favorable factors in the practice of the third aspect of the invention.

In the practice of the first, second or third aspect of the invention, the content of reduced coenzyme $Q_{10}$ is not particularly restricted but, in view of the stability and ease or convenience of use of reduced coenzyme $Q_{10}$, and the like, it is, for example, generally higher than 3% by weight, preferably higher than 5% by weight, more preferably higher than 6% by weight, still more preferably higher than 7% by weight, particularly preferably higher than 8% by weight, relative to the whole composition. The upper limit is not particularly restricted but, in view of the liquid characteristics, for example, it is generally not higher than 50% by weight, preferably not higher than 30% by weight, more preferably not higher than 20% by weight, relative to the whole composition.

The composition of the invention may be a composition containing externally added reduced coenzyme $Q_{10}$ or may be a composition containing reduced coenzyme $Q_{10}$ as obtained by reducing oxidized coenzyme $Q_{10}$ in the above-mentioned fat and oil and/or polyol, or in the fat and oil and/or polyol containing the polyglycerol fatty acid ester, using such a reducing agent as sodium dithionite (sodium hydrosulfite) or an ascorbic acid. It is preferred, however, that the composition be substantially free of any oxidation product derived from the reducing agent used for the reduction of oxidized coenzyme $Q_{10}$.

Generally, compositions containing externally added reduced coenzyme $Q_{10}$, namely compositions prepared by using reduced coenzyme $Q_{10}$ separately produced, are preferred since the set of components of the composition can be simplified and the compositions can be prepared with ease.

In cases where the following oral dosage forms are prepared from the composition of the invention, it is more preferable that the composition be in a liquid form (inclusive of not only the solution form but also the suspension or slurry form) at ordinary temperature or at higher temperatures.

Although the composition of the present invention may be used as it is, it may preferably be used in oral administration forms such as a capsule (a hard capsule, a soft capsule), a tablet, syrup and a drink by a further process. Moreover, forms such as cream, a suppository, toothpaste, etc. by a further process may also be applicable. Particularly preferred is a capsule, and most preferred is a soft capsule. A capsule material is not particularly restricted, and typically includes gelatin derived from a beef bone, oxhide, a pig skin, a fish skin, etc., and also includes other materials (e.g. thickening stabilizers for example seaweed-derived products such as carrageenan, alginic acid and the like, vegetable seed-derived products such as locust bean gum and guar gum, etc., and agents for manufacturing including celluloses) which are usable as food additives.

The capsules can be packed in phials, bottles, plastic bags, aluminum laminate bags and the like. Furthermore they can be put up PTP packages, three side sealed packages, four side sealed packages, strip packages, aluminum shaping packages, stick packages and the like.

For maximizing the effects of the present invention, it is preferable, for example, that the method of the invention be carried out and the composition of the invention be prepared and/or stored in a deoxygenized atmosphere such as an inert gas atmosphere, for example a nitrogen or the like atmosphere. It is also preferable that the above-mentioned processing and the storage after processing be carried out in the deoxygenized atmosphere such as an inert gas atmosphere mentioned above.

When the composition and method of preparation as mentioned above are employed, the protective effect against oxidation of the fat and oil and/or polyol is not substantially impaired and it can be expected that compositions showing a reduced coenzyme $Q_{10}$ retention percentage of not lower than 95%, preferably not lower than 96%, more preferably not lower than 97%, can be obtained in accordance with the first and second aspect of the invention and, in accordance with the third aspect of the invention, compositions showing a reduced coenzyme $Q_{10}$ retention percentage of not lower than 70%, preferably not lower than 80%, more preferably not lower than 90%, can be obtained, as compared with compositions containing no other components than the fat and oil and/or polyol.

In accordance with the invention, reduced coenzyme $Q_{10}$ can be adequately protected from oxidation and, further, compositions in which the oxidation product derived from a reducing agent, for example dehydroascorbic acid or the like, is absent can be provided. Furthermore, compositions showing high in absorbability in the living body of reduced coenzyme $Q_{10}$ can also be provided.

BEST MODE FOR CARRYING OUT THE INVENTION

The following production examples, working examples, comparative examples and reference examples illustrate the present invention in further detail. They are, however, by no means limitative of the scope of the invention. The purity and reduced coenzyme $Q_{10}$/oxidized coenzyme $Q_{10}$ ratio (weight ratio) were determined by the following HPLC analysis.
(HPLC Conditions)
Column; SYMMETRY C18 (product of Waters), 250 mm (in length), 4.6 mm (in inside diameter): mobile phase; $C_2H_5OH/CH_3OH=4/3$ (v/v): detection wavelength; 210 nm: flow rate; 1 ml/min: retention time of reduced coenzyme $Q_{10}$; 9.1 min: retention time of oxidized coenzyme $Q_{10}$; 13.3 min.

Production Example 1

Oxidized coenzyme $Q_{10}$ (100 g) was dissolved in 1000 g of heptane at 25° C. While stirring (stirring power consumption: 0.3 kW/m³), an aqueous solution prepared by dissolving 100 g of sodium dithionite (purity: at least 75%), as a reducing agent, in 1000 ml of water was gradually added thereto, and a reduction reaction was carried out at 25° C. and at a pH between 4 and 6. After the lapse of 2 hours, an aqueous phase was removed from the reaction mixture, and the heptane phase was washed for 6 times with 1000 g of deaerated saturated brine. This heptane phase was cooled to 2° C. while stirring (stirring power consumption: 0.3 kW/m³) to give a white slurry. All the operations were carried out in a nitrogen atmosphere. The slurry obtained was filtered under reduced pressure, and the wet crystal was washed in sequence with cold heptane, cold ethanol, cold water, cold ethanol and cold heptane (the temperature of cold solvents used for washing: 2° C.). The wet crystal was further dried under reduced pressure (20 to 40° C., 1 to 30 mmHg) to give 93 g of a white dry crystal (yield: 92.8 mole %). The weight ratio of reduced coenzyme $Q_{10}$/oxidized coenzyme $Q_{10}$ of the crystal obtained was 99.6/0.4.

Production Example 2

To 1000 g of ethanol, 100 g of oxidized coenzyme $Q_{10}$ and 60 g of ascorbic acid were added, and the mixture was stirred at 78° C. to carry out a reduction reaction. After the lapse of 30 hours, the mixture was cooled to 50° C. and was added with 330 g of ethanol and 70 g of water while maintaining the same temperature. This ethanol solution was cooled to 2° C. at a cooling rate of 10° C./hour while stirring (stirring power consumption: 0.3 kW/m³) to give a white slurry. The slurry showed very good fluidity and was easily brushed away from a crystallization container. The slurry obtained was filtered under reduced pressure, and the wet crystal was washed in sequence with cold ethanol, cold water and cold ethanol (the temperature of cold solvents used for washing: 2° C.). The wet crystal was further dried under reduced pressure (20 to 40° C., 1 to 30 mmHg) to give 97 g of a white dry crystal (isolated product yield: 97 mole %). All the operations were carried out in a nitrogen atmosphere. The weight ratio of reduced coenzyme $Q_{10}$/oxidized coenzyme $Q_{10}$ of the crystal obtained was 99.5/0.5.

Examples 1 to 3 and Comparative Example 1

The crystals obtained in Production Example 1 were added to soybean oil, glycerol, and a mixture thereof, respectively, to a concentration of 6% by weight, and the resulting mixtures were stored in the air at 40° C. under a light-shielded condition for 3 days, and the reduced coenzyme $Q_{10}$/oxidized coenzyme $Q_{10}$ weight ratios in the solutions were determined. The results are shown in Table 1 together with the results obtained for comparison by storing the crystals alone under the conditions mentioned above.

TABLE 1

|  |  | Reduced coenzyme $Q_{10}$/oxidized coenzyme $Q_{10}$ weight ratio |
| --- | --- | --- |
| Example 1 | Soybean oil | 97.5/2.5 |
| Example 2 | Glycerol | 95.3/4.7 |
| Example 3 | Soybean oil/glycerol = 8/2 (weight ratio) | 96.8/3.2 |
| Compar. Ex. 1 | Crystals | 75.0/25.0 |

Examples 4 to 7

The crystals obtained in Production Example 1 were added to various fats and oils specified in Table 2, respectively, to a concentration of 6% by weight, and the resulting mixtures were stored in the air at 40° C. under a light-shielded condition for 3 days, and the reduced coenzyme $Q_{10}$/oxidized coenzyme $Q_{10}$ weight ratios in the solutions were determined. The results are shown in Table 2. The medium-chain fatty acid triglyceride used had a $C_8$ proportion of 60% and a $C_{10}$ proportion of 40%.

TABLE 2

| Example | Fat and oil | Reduced coenzyme $Q_{10}$/oxidized coenzyme $Q_{10}$ weight ratio |
|---|---|---|
| 4 | Soybean oil | 97.5/2.5 |
| 5 | Safflower oil | 95.2/4.8 |
| 6 | Coconut oil | 98.0/2.0 |
| 7 | Palm oil | 97.2/2.8 |
| 8 | Rapeseed oil | 97.8/2.2 |
| 9 | Rice oil | 97.0/3.0 |
| 10 | Peanut oil | 96.8/3.2 |
| 11 | Wheat germ oil | 96.5/3.5 |
| 12 | Lard | 96.4/3.6 |
| 13 | Milk fat | 97.5/2.5 |
| 14 | Perilla oil | 97.2/2.8 |
| 15 | Hydrogenated fish oil | 97.5/2.5 |
| 16 | Cottonseed oil | 97.4/2.6 |
| 17 | Medium-chain fatty acid triglyceride | 97.1/2.9 |

Comparative Example 2

The crystals obtained in Production Example 1 were added to olive oil to a concentration of 6% by weight, and the resulting mixture was stored in the air at 40° C. under a light-shielded condition for 3 days. The reduced coenzyme $Q_{10}$/oxidized coenzyme $Q_{10}$ weight ratio in the solution after storage was 92.3/7.7.

Examples 18 and 19 and Comparative Example 3

Compositions containing the crystals obtained in Production Example 1, soybean oil and vitamin E according to the compositions given below were prepared. These were stored in the air at 40° C. under a light-shielded condition for 3 days, and the reduced coenzyme $Q_{10}$/oxidized coenzyme $Q_{10}$ weight ratios in the solutions were then determined. The results are shown in Table 3.

a) Content of reduced coenzyme $Q_{10}$ in the composition: 4.42% by weight,
Vitamin E content based on the system excluding coenzyme $Q_{10}$: 0.00% by weight;

b) Content of reduced coenzyme $Q_{10}$ in the composition: 4.42% by weight,
Vitamin E content based on the system excluding coenzyme $Q_{10}$: 1.00% by weight;

c) Content of reduced coenzyme $Q_{10}$ in the composition: 4.42% by weight,
Vitamin E content based on the system excluding coenzyme $Q_{10}$: 4.11% by weight.

TABLE 3

| | Vitamin E content (wt %) | Reduced coenzyme $Q_{10}$/oxidized coenzyme $Q_{10}$ weight ratio |
|---|---|---|
| Example 18 | 0.0 | 97.2/2.8 |
| Example 19 | 1.0 | 95.5/4.5 |
| Compar. Ex. 3 | 4.11 | 92.1/7.9 |

Comparative Example 4

A composition containing the crystals obtained in Production Example 1, soybean oil and vitamin E according to the composition given below was prepared and stored in the air at 40° C. under a light-shielded condition for 3 days.

Content of reduced coenzyme $Q_{10}$ in the composition: 5.19% by weight,

Vitamin E content based on the system excluding coenzyme $Q_{10}$: 4.11% by weight.

The reduced coenzyme $Q_{10}$/oxidized coenzyme $Q_{10}$ weight ratio in the solution after storage was 92.9/7.1.

Examples 20 to 22 and Comparative Examples 5 to 8

The crystals obtained in Production Example 1 were added to the fat and oil and/or surfactants specified in Table 4, respectively, to a concentration of 6% by weight, and the resulting mixtures were stored in the air at 40° C. under a light-shielded condition for 3 days, and the reduced coenzyme $Q_{10}$/oxidized coenzyme $Q_{10}$ weight ratios in the solutions were then determined. The results are shown in Table 4. The medium-chain fatty acid triglyceride (MCT) used had a $C_8:C_{10}$ ratio of 6:4, and the Tween 80 and Span 80 used as surfactant were both the products of Nakalai Tesque Inc.

TABLE 4

| | Fat and oil and/or surfactant | Reduced coenzyme $Q_{10}$/oxidized coenzyme $Q_{10}$ weight ratio |
|---|---|---|
| Example 20 | Soybean oil | 97.5/2.5 |
| Example 21 | Medium-chain fatty acid triglyceride(MCT) | 97.1/2.9 |
| Example 22 | MCT/lecithin = 90/10 | 96.5/3.5 |
| Compar. Ex. 5 | Soybean oil/Tween80 = 25/75 | 20.1/79.9 |
| Compar. Ex. 6 | MCT/Tween80 = 25/75 | 15.0/85.0 |
| Compar. Ex. 7 | MCT/Span80 = 25/75 | 65.6/34.4 |
| Compar. Ex. 8 | Span 80 | 64.8/35.2 |

Examples 23 and 24 and Comparative Examples 9 and 10

90 parts of medium-chain fatty acid triglyceride (MCT; $C_8:C_{10}=6:4$) and 10 parts of one of the surfactants specified in Table 5 (diglycerol monooleate; Riken Vitamin Co., Ltd.'s Poem DO-100V: diglycerol monolaurate; Taiyo Kagaku Co., Ltd.'s Sunsoft Q-12D) were mixed up with stirring, and the crystals obtained in Production Example 2 were dissolved in the mixture at 40° C. to a concentration of 3% (w/v). After 3 days of storage in the air at 40° C. under a light-shielded condition, the reduced coenzyme $Q_{10}$/oxidized coenzyme $Q_{10}$ weight ratio in each solution was determined. The results thus obtained are shown in Table 5.

TABLE 5

|  | Surfactant | Reduced coenzyme $Q_{10}$/oxidized coenzyme $Q_{10}$ weight ratio |
|---|---|---|
| Example 23 | Diglycerol monooleate | 95.5/4.5 |
| Example 24 | Diglycerol monolaurate | 90.1/9.9 |
| Compar. Ex. 9 | Tween80 | 30.5/69.5 |
| Compar. Ex. 10 | Span80 | 56.6/43.4 |

Example 25 and Comparative Examples 11 and 12

Rice oil (80 parts by weight) and 20 parts by weight of one of the surfactants specified in Table 6 (diglycerol monooleate; Riken Vitamin Co., Ltd.'s Poem DO-100V: monoglycerol monooleate; Taiyo Kagaku Co., Ltd.'s Sunsoft No. 0-30: condensed ricinolic acid-tetraglycerol; Sunsoft No. 818) were mixed up with stirring, the crystals obtained in Production Example 2 were dissolved in the mixture at 40° C. to a concentration of 3% (w/v). After 3 days of storage in the air at 40° C. under a light-shielded condition, the reduced coenzyme $Q_{10}$/oxidized coenzyme $Q_{10}$ weight ratio in each solution was determined. The results thus are shown in Table 6.

TABLE 6

|  | Surfactant | Reduced coenzyme $Q_{10}$/oxidized coenzyme $Q_{10}$ weight ratio |
|---|---|---|
| Example 25 | Diglycerol monooleate | 95.2/4.8 |
| Compar. Ex..11 | Monoglycerol monooleate | 51.2/48.8 |
| Compar. Ex..12 | Condensed ricinolic acid-tetraglycerol | 48.3/51.7 |

Example 26

The crystals obtained in Production Example 1 and ascorbyl palmitate were added, each to a concentration of 4% by weight, to a composition composed of 80 parts by weight of medium-chain fatty acid triglyceride (MCT; $C_8$: $C_{10}$=6:4), 10 parts by weight of Span 80 and 10 parts by weight of diglycerol monooleate (Riken Vitamin Co., Ltd.'s Poem DO-100V). After 3 days of storage in the air at 40° C. under a light-shielded condition, the reduced coenzyme $Q_{10}$/oxidized coenzyme $Q_{10}$ weight ratio in the solution was 99.6/0.4.

Reference Example 1

The fat and oil specified in Table 7 were used as base materials. Separately, base materials were prepared by adding 10 parts by weight of one of the polyglycerol fatty acid esters specified in Table 7 (diglycerol monooleate; Riken Vitamin Co., Ltd.'s Poem DO-100V: diglycerol monolaurate; Taiyo Kagaku Co., Ltd.'s Sunsoft Q-12D) to 90 parts of the fat and oil specified in Table 7. The crystals obtained in Production Example 2 were dissolved in the base materials in a nitrogen atmosphere at 40° C. to a concentration of 3% (w/v). Each solution obtained was orally administered to rats, the reduced coenzyme $Q_{10}$ concentration in plasma were determined, and the AUC (area under the blood concentration-time curve) until hour 4 after administration was calculated. The results thus obtained are shown in Table 7. From the results, it is evident that the addition of polyglycerol fatty acid esters results in improved in absorbability in the living body.

TABLE 7

| Fat and oil | Surfactant | AUC(μg/ml*h) |
|---|---|---|
| MCT | Diglycerol monooleate | 9.12 |
| Rice oil | Diglycerol monooleate | 9.69 |
| MCT | Diglycerol monolaurate | 8.37 |
| MCT | None | 7.25 |
| Rice oil | None | 4.54 |

Reference Example 2

The crystals obtained in Production Example 2 were dissolved in Tween 80 in a nitrogen atmosphere at 40° C. to a concentration of 3% (w/v). The solution obtained was orally administered to rats, the reduced coenzyme $Q_{10}$ concentration in plasma were determined, and the AUC (area under the blood concentration-time curve) until hour 4 after administration was calculated and found to be 2.26 μg/ml*h.

Reference Example 3

The solubility of the crystals obtained in Production Example 1 in medium-chain fatty acid triglyceride (MCT, $C_8$:$C_{10}$=6:4), soybean oil, safflower oil, or rice oil at 30° C. is shown in Table 8.

TABLE 8

| Fat and oil | Soybean oil | Safflower oil | Rice oil | MCT |
|---|---|---|---|---|
| Solubility (wt %) | 10.9 | 11.1 | 10.2 | 22.4 |

The crystals obtained in Production Example 1 were added to soybean oil to a concentration of 6% by weight, and gelatin soft capsules were obtained in the conventional manner.

Example 28

The crystals obtained in Production Example 1 were added to perilla oil to a concentration of 6% by weight, and gelatin soft capsules were obtained in the conventional manner.

Example 29

The crystals obtained in Production Example 2 were added to a mixture of medium-chain fatty acid triglyceride (MCT, $C_8$:$C_{10}$=6:4) and diglycerol monooleate at 50° C., and gelatin soft capsules were obtained in the conventional manner, according to the following formulation:

| Reduced coenzyme $Q_{10}$ | 60 parts by weight |
|---|---|
| Diglycerol monooleate | 100 parts by weight |
| Medium-chain fatty acid triglyceride | 840 parts by weight |

Example 30

The crystals obtained in Production Example 2 were added to a mixture of medium-chain fatty acid triglyceride (MCT, $C_8$:$C_{10}$=6:4), diglycerol monooleate (Riken Vitamin Co., Ltd.'s Poem DO-100V), Span 80 and ascorbyl palmitate at 50° C., and gelatin soft capsules were obtained in the conventional manner, according to the following formulation:

| | |
|---|---|
| Reduced coenzyme $Q_{10}$ | 60 parts by weight |
| Diglycerol monooleate | 100 parts by weight |
| Span 80 | 100 parts by weight |
| Ascorbyl palmitate | 60 parts by weight |
| Medium-chain fatty acid triglyceride | 680 parts by weight |

Example 31

The crystals obtained in Production Example 1 were added to a mixture of medium-chain fatty acid triglyceride (MCT, $C_8:C_{10}=6:4$), lecithin and ascorbyl palmitate at 50° C., and gelatin soft capsules were obtained in the conventional manner, according to the following formulation:

| | |
|---|---|
| Reduced coenzyme $Q_{10}$ | 40 parts by weight |
| Lecithin | 180 parts by weight |
| Ascorbyl palmitate | 40 parts by weight |
| Medium-chain fatty acid triglyceride | 740 parts by weight |

Example 32

The crystals obtained in Production Example 2 were added to a mixture of rice oil, hydrogenated oil, beeswax (viscosity modifier) and lecithin, and gelatin soft capsules were obtained in the conventional manner, according to the following formulation:

| | |
|---|---|
| Reduced coenzyme $Q_{10}$ | 60 parts by weight |
| Rice oil | 690 parts by weight |
| Hydrogenated oil | 170 parts by weight |
| Beeswax | 60 parts by weight |
| Lecithin | 20 parts by weight |

Example 33

The crystals obtained in Production Example 2 were added to a mixture of rice oil, diglycerol monooleate (Riken Vitamin Co., Ltd.'s Poem DO-100V), hydrogenated oil, beeswax and lecithin, and gelatin soft capsules were obtained in the conventional manner, according to the following formulation:

| | |
|---|---|
| Reduced coenzyme $Q_{10}$ | 100 parts by weight |
| Diglycerol monooleate | 70 parts by weight |
| Rice oil | 580 parts by weight |
| Hydrogenated oil | 170 parts by weight |
| Beeswax | 60 parts by weight |
| Lecithin | 20 parts by weight |

Example 34

The crystals obtained in Production Example 2 were added to a mixture of rapeseed oil, diglycerol monooleate (Riken Vitamin Co., Ltd.'s Poem DO-100V), hydrogenated oil, beeswax and lecithin, and gelatin soft capsules were obtained in the conventional manner, according to the following formulation:

| | |
|---|---|
| Reduced coenzyme $Q_{10}$ | 100 parts by weight |
| Diglycerol monooleate | 320 parts by weight |
| Rapeseed oil | 330 parts by weight |
| Hydrogenated oil | 170 parts by weight |
| Beeswax | 60 parts by weight |
| Lecithin | 20 parts by weight |

Example 35

The crystals obtained in Production Example 2 were added to a mixture of Ematech (Riken Vitamin Co., Ltd.'s diglycerol monooleate-containing oil), hydrogenated oil, beeswax and lecithin, and gelatin soft capsules were obtained in the conventional manner, according to the following formulation:

| | |
|---|---|
| Reduced coenzyme $Q_{10}$ | 100 parts by weight |
| Ematech | 650 parts by weight |
| Hydrogenated oil | 170 parts by weight |
| Beeswax | 60 parts by weight |
| Lecithin | 20 parts by weight |

Example 36

The crystals obtained in Production Example 2 were added to a mixture of medium-chain fatty acid triglyceride (MCT, $C_8:C_{10}=6:4$), diglycerol monooleate (Riken Vitamin Co., Ltd.'s Poem DO-100V), Span 80, ascorbyl palmitate, hydrogenated oil, beeswax and lecithin, and gelatin soft capsules were obtained in the conventional manner, according to the following formulation:

| | |
|---|---|
| Reduced coenzyme $Q_{10}$ | 100 parts by weight |
| Diglycerol monooleate | 100 parts by weight |
| Span 80 | 100 parts by weight |
| Ascorbyl palmitate | 100 parts by weight |
| Medium-chain fatty acid triglyceride | 350 parts by weight |
| Hydrogenated oil | 170 parts by weight |
| Beeswax | 60 parts by weight |
| Lecithin | 20 parts by weight |

Example 37

The gelatin soft capsules obtained in Example 30, Example 32 and Example 34 were placed in glass bottles and, after tight closure in the presence of air, stored at 25° C. under a light-shielded condition (at the start of storage, the reduced coenzyme $Q_{10}$/oxidized coenzyme $Q_{10}$ weight ratio was 98.5/1.5 in all gelatin soft capsules). After 6 months of storage, the reduced coenzyme $Q_{10}$/oxidized coenzyme $Q_{10}$ weight ratios in the gelatin soft capsules were determined. The results thus obtained are shown in Table 9.

TABLE 9

| | Reduced coenzyme $Q_{10}$/ oxidized coenzyme $Q_{10}$ weight ratio |
|---|---|
| Soft capsules of Example 30 | 98.4/1.6 |
| Soft capsules of Example 32 | 98.1/1.9 |
| Soft capsules of Example 34 | 98.0/2.0 |

INDUSTRIAL APPLICABILITY

The present invention, which has the constitution described hereinabove, can provide a simple and appropriate method for protecting reduced coenzyme $Q_{10}$ against oxidation and maintaining the same stably and composition therefor.

The invention claimed is:

1. A reduced coenzyme $Q_{10}$-containing composition which comprises reduced coenzyme $Q_{10}$, a polyglycerol fatty acid ester, wherein the degree of polymerization of glycerol in said polyglycerol fatty acid ester is 2 to 10, and at least one member selected from the group consisting of a fat component, an oil component and a polyol,
   wherein a content of the at least one member selected from the group consisting of a fat component, an oil component and a polyol is not lower than 50% by weight based on total weight of the composition minus a weight of coenzyme $Q_{10}$; a content of the polyglycerol fatty acid ester is not lower than 1% by weight and not higher than 40% by weight based on total weight of the composition minus a weight of coenzyme $Q_{10}$;
   a content of Tween and/or Span species, when the same is further contained in the composition, is not higher than 30% by weight based on total weight of the composition minus a weight of coenzyme $Q_{10}$; and wherein the fat component or oil component is at least one member selected from the group consisting of coconut oil, palm oil, palm kernel oil, linseed oil, camellia oil, brown rice germ oil, avocado oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil, olive oil, lard, milk fat, fish oil, beef tallow, modified fat component, modified oil component, medium-chain fatty acid triglycerides, fatty acid partial glycerides, and phospholipids,
   wherein the modified fat component or modified oil component is derived from at least one member selected from the group consisting of coconut oil, palm oil, palm kernel oil, linseed oil, camellia oil, brown rice germ oil, avocado oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil, olive oil, lard, milk fat, fish oil, and beef tallow by a process selected from the group consisting of fractionation, hydrogenation and transesterification; and
   wherein a percent retention of reduced coenzyme $Q_{10}$ after 3 days storage in the air at 40° C. under a light-shielded condition is not lower than 70%, with the percent retention in the corresponding composition composed of reduced coenzyme $Q_{10}$, and at least one member selected from the group consisting of the fat component, the oil component and the polyol alone after storage under the same conditions being taken as 100%.

2. The composition according to claim 1, wherein the polyol comprises at least one polyol selected from among glycerol, propylene glycol and polyethylene glycol.

3. The composition according to claim 1 which further comprises an ascorbic acid.

4. The composition according to claim 3, wherein the content of the ascorbic acid is not higher than 30% by weight based on the total weight of the composition minus a weight of coenzyme $Q_{10}$.

5. The composition according to claim 3 which further comprises a surfactant other than polyglycerol fatty acid esters.

6. The composition according to claim 5, wherein the surfactant other than polyglycerol fatty acid esters is a Tween or Span species.

7. The composition according to claim 5, wherein the content of the surfactant other than polyglycerol fatty acid esters is not higher than 90% by weight based on the total weight of the composition minus a weight of coenzyme $Q_{10}$.

8. The composition according to claim 1, wherein the polyglycerol fatty acid ester is represented by the following formula (1):

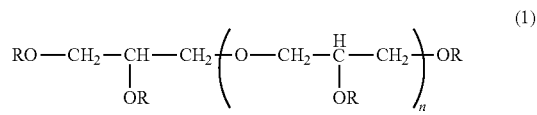

in the formula, n represents an integer of 1 to 9 and the four R's each independently represents a fatty acid residue containing 2 to 22 carbon atoms or a hydrogen atom, exclusive of the case where all R's are hydrogen atoms.

9. The composition according to claim 1, wherein the polyglycerol fatty acid ester has an HLB value of 4 to 12.

10. The composition according to claim 1, wherein the fatty acid residue or residues in the polyglycerol fatty acid ester each contains not less than 8 carbon atoms.

11. The composition according to claim 1, wherein the content of reduced coenzyme $Q_{10}$ in the composition is higher than 5% by weight.

12. The composition according to claim 1, wherein the reduced coenzyme $Q_{10}$ is an externally added one.

13. The composition according to claim 1, wherein the ratio of number of fatty acid residues in polyglycerol fatty acid ester to degree of polymerization of glycerol is 1/4 to 1/2.

14. The composition according to claim 1, wherein the polyglycerol fatty acid ester is a diglycerol fatty acid ester.

15. The composition according to claim 14, wherein the diglycerol fatty acid ester comprises at least one species selected from among diglycerol monocaprate, diglycerol monolaurate, and diglycerol monooleate.

16. The composition according to claim 15, wherein the diglycerol fatty acid ester is diglycerol monooleate.

17. The composition according to claim 1 which is prepared or stored in a deoxygenized atmosphere.

18. The composition according to claim 1 which is processed in an oral dosage form.

19. The composition according to claim 18, said dosage form being capsules.

20. The composition according to claim 19, said capsules being soft capsules.

21. The composition according to claim 19, said capsules being packed in a phial, bottle, plastic bag, aluminum laminate bag, PTP packaging, three side-sealed packaging, four side-sealed packaging, strip packaging, aluminum shaped packaging or stick packaging.

22. The composition according to claim 1, wherein a content of vitamin E, when the same is further contained in the composition, is lower than 4% by weight based on total weight of the composition minus a weight of coenzyme $Q_{10}$.

23. The composition according to claim 1, which comprises reduced coenzyme $Q_{10}$, the polyglycerol fatty acid ester, and at least one member selected from the group consisting of the fat component and the oil component.

24. The composition according to claim 1, wherein the content of reduced coenzyme $Q_{10}$ in the composition is not higher than 30% by weight.

25. The composition according to claim 1, wherein the polyglycerol fatty acid ester is represented by the following formula (1):

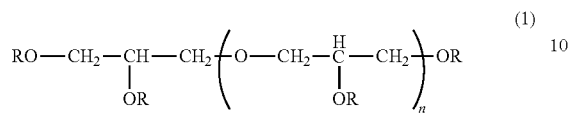

in the formula, n represents an integer of 1 to 9, one of the R's represent a fatty acid residue containing 2 to 22 carbon atoms and the rest of the R's each represents a hydrogen atom.

* * * * *